United States Patent [19]

Uemura et al.

[11] Patent Number: 5,173,407

[45] Date of Patent: Dec. 22, 1992

[54] METHOD FOR MEASURING GLYCOSYLTRANSFERASE

[75] Inventors: Morito Uemura; Shin-ya Yoshida, both of Hino, Japan

[73] Assignee: Konica Corporation, Tokyo, Japan

[21] Appl. No.: 643,695

[22] Filed: Jan. 22, 1991

Related U.S. Application Data

[63] Continuation of Ser. No. 131,669, Dec. 11, 1987, abandoned.

[30] Foreign Application Priority Data

Dec. 16, 1986 [JP] Japan ................................ 61-299333

[51] Int. Cl.$^5$ .......................... C12Q 1/48; G01N 33/53
[52] U.S. Cl. ......................................... 435/15; 435/7.1; 436/101; 436/548; 436/827
[58] Field of Search ................... 435/7.1, 15; 436/827, 436/548, 101

[56] References Cited

U.S. PATENT DOCUMENTS

| | | | |
|---|---|---|---|
| 4,261,976 | 4/1981 | Isselbacher et al. | 435/177 |
| 4,371,515 | 2/1983 | Chu | 436/827 |
| 4,515,890 | 5/1985 | Manderino et al. | 435/7 |
| 4,755,460 | 7/1988 | Bostwick et al. | 435/7 |
| 4,770,994 | 9/1988 | Rittenhouse | 435/15 |

FOREIGN PATENT DOCUMENTS

WO80/02296 10/1980 PCT Int'l Appl. .................. 435/15

OTHER PUBLICATIONS

Young et al, J. Biol. Chem. vol. 256(21) pp. 10967–10972, year 1981.
Tsumori et al, Boei Ika Daigakko Shingoku Katei Kenkyu Kiyo, vol. 9, pp. 179–188 year 1986 CA 105(11) 93802n.

Primary Examiner—David L. Lacey
Assistant Examiner—Laurie Scheiner
Attorney, Agent, or Firm—Finnegan, Henderson, Farabow, Garrett and Dunner

[57] ABSTRACT

There is disclosed a method for measuring a glycosyltransferase, for measuring an activity or a concentration of the glycosyltransferase for a specific sugar, which comprises using a constitution containing a donor which is not labelled and a substance which is specifically bound only to a product.

10 Claims, 1 Drawing Sheet

METHOD FOR MEASURING GLYCOSYLTRANSFERASE

This is a continuation of application Ser. No. 07/131,699, filed Dec. 11, 1987, now abandoned.

BACKGROUND OF THE INVENTION

This invention relates to a method for measuring a process for forming sugar chains which participates in metabolism or maintenance of the living body, particularly to a method for measuring glycosyltransferase.

Glycosyltransferase is a basic enzyme widely distributed in organisms from higher animals including human beings to yeasts or bacteria, and it has been said to be an enzyme which participates in biosynthesis of sugar chains in glycoproteins, glycolipids and is responsible for an important role in metabolic maintenance of the living body. On the other hand, it has been reported to exist widely in cytoplasms of higher animals including human beings, primarily in Golgi apparatus, cell membranes and blood.

Also, in recent years, physiological activity of the sugar chain itself, particularly in cell-cell recognition is of foremost interest. Above all, aberrant glycosylation in transformation is furnishing a great topic from the standpoint of tumor markers. The sugar chain sequence and its bonding mode in such sugar chains or oligosugars are formed specifically by glycosyltransferase depending on individual sugars, while on the contrary specificity of glycosyltransferase has been considered to participate greatly in characterizing the sugar chain.

In view of such background, measurement of glycosyltransferase may be said to have an important position not only in basic research of life science but also in applications for medicine or clinical chemistry.

On the other hand, methods for measuring glycosyltransferase up to date have generally been the method in which the sugar moiety of the sugar nucleotide which is the donor is labelled with $^3H$, $^{14}C$, and the radioactivity of the acceptor to which its sugar is transferred by glycosyltransferase is measured.

In the present specification, the donor means a substance having been bound to the sugar to be transferred by glycosyltransferase. The acceptor means a substance of which sugar is to be transferred by glycosyltransferase, and the product means a substance in which sugar is transferred to the acceptor by glycosyltransferase.

The above method has two drawbacks:

(1) the labelled sugar nucleotide is limited to $^3H$ and $^{14}C$, and the donor labelled by $^3H$ or $^{14}C$ is expensive and unstable as well as low in sensitivity. Consequently liquid scintillation measurement is required; and (2) during separation of the acceptor containing the transferred labelled sugar from the labelled sugar nucleotide, operation such as salting-out, washing, electrophoresis, etc. are required.

The problems in operability and cost have which inhibited wide generalization of this method in clinical tests, etc.

In order to solve these problems, several attempts have been done. In Analy. Biochem. 102, 441 (1980), there is disclosed the method in which, instead of labelling sugar, the nucleotide formed by transfer of sugar is via plural enzymatic reactions finally measured by colorimetry or fluorescent intensity.

However, this method is deficient in sensitivity as compared with the prior art methods.

Also, in Analy. Biohem. 155, 395 (1986), in order to solve above drawback (2), choleratoxin capable of being specifically bound to the acceptor to which the sugar is transferred is used, but this method is devoid of general applicability for glycosyltransferases in general, and also the above drawback (1) has not been solved.

SUMMARY OF THE INVENTION

An object of the present invention is to provide a measuring method which is widely applicable for glycosyltransferases and has solved the above drawbacks (1) and (2) at the same time.

The above drawbacks, can be solved by a method for measuring glycosyltransferase of the present invention, by using a composition which comprises:

(i) a sugar nucleotide which is not labelled and which is a donor, and (ii) a substance which is bound specifically only to the acceptor to which said sugar is transferred, therefore only to the product.

DESCRIPTION OF THE PREFERRED EMBODIMENTS

Figure 1:
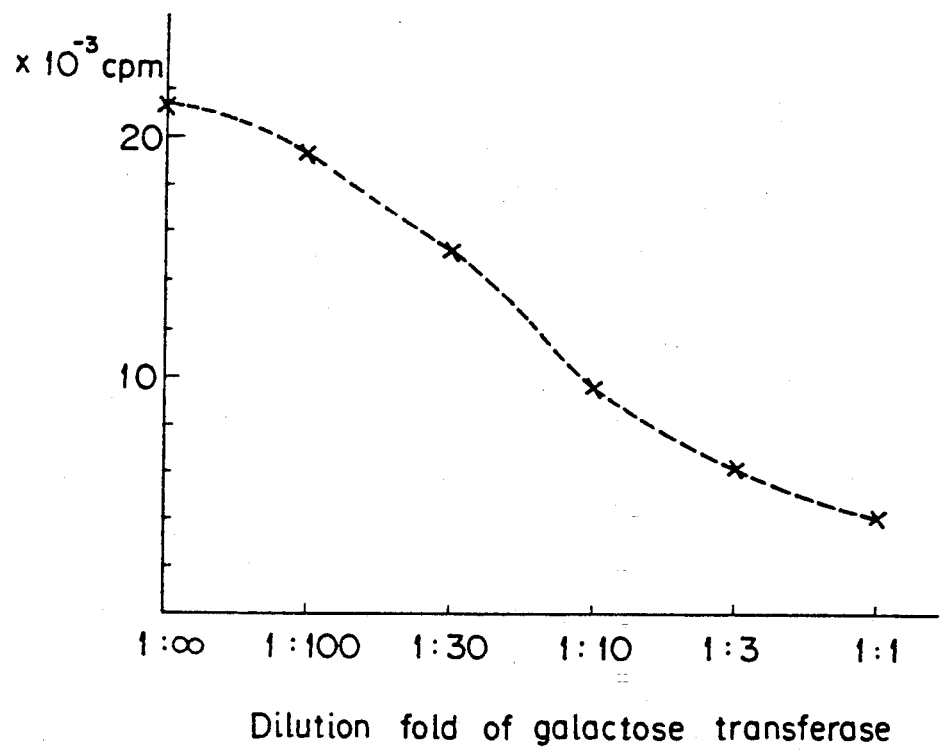
FIG. 1 shows a result of radioactivity of the present invention and FIG. 2 shows a comparative sample.
Figure 2:
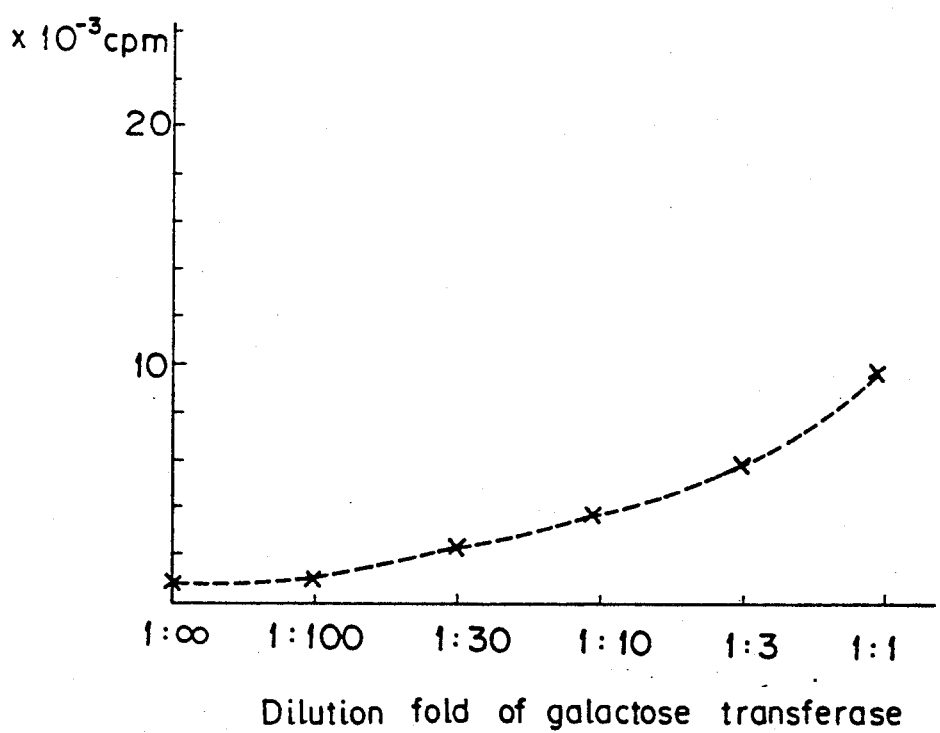

The glycosyltransferase as mentioned in the present invention may include, for example, galactosyltransferase, fucosyltransferase, sialyltransferase, mannosyltransferase, N-acetylglucosamyltransferase, N-acetylgalactosamyltransferase, etc. These enzymes are inclusive of some enzymes with trapping specificities for sugars with different binding modes.

As the sugar nucleotide, there may be included, for example uridine diphosphate (UDP)-sugar, cytidine monophosphate (CMP)-sugar, cytidine diphosphate (CDP)-sugar, guanosine diphosphate (GDP)-sugar, adenine diphosphate (ADP)-sugar, etc., and the combination with nucleotide can be determined depending on the sugar.

As the acceptor, there may be included monosaccharides, oligosaccharides, and glycoproteins and glycolipids of those sugars. The sugars of the above acceptors and the terminal sugars of said glycolipids are defined by the respective glycosyltransferases.

In the present invention, the substance which is bound specifically only to the acceptor to which the sugar to be transferred has been linked by transfer may include specifically, for example, an antibody or a lectin. As the necessary condition for these specifically bound substances, they must be bound specifically only to the acceptor to which the sugar is transferred, without binding to the sugar nucleotide which is the donor and the original acceptor to which said sugar is to be transferred.

In the case of an antibody, it can be transferred with a specific glycosyltransferase to be immunized with a glycoprotein, glycolipid, etc, having a sugar at the non-reducing terminal end. Preferably, a monoclonal antibody is advantageous from the aspect of specificity. Actually, some monoclonal antibodies recognizing various non-reducing terminal sugars have been obtained (Cell Engineering, Vol. 5, No. 7, page 665 (1986)).

In the case of lectins, there have been various reports about reactivities on respective sugars (edited by Toshiaki Osawa: Lectin and Cell Biology, Kodansha, (1985)). For example, for galactosyltransferase forming Galβ1-3GalNAc[T] (where [T] represents a chain), *Agaricus bisporus* (ABA), *Maclura pomifera* (MPA) is suitable as lectin, while for galactosyltransferase forming Galβ1-4GlcNAc[T], *Ricinus communis-I* (RCA-I) is suitable. For N-acetylglucosamyltransferase forming GlcNAc terminal, *Triticum vulgaris* (WGA), *Oryza satira* (OSA) may be included; for sialyltransferase for sialic acid, *Limulus polyphemus* (LPA) may be included; for mannosyltransferase, *Canavalia ensiformis* (ConA), *Pisum sativum* (PEA) may be included; anf for N-acetylgalactosamyltransferase, *Dilichos biflorus* (DBA) may be included. The above-mentioned are merely exemplary, and the present invention is not limited to these.

An example of the method for measuring glycosyltransferase which has been the most generalized up to date is described.

(1) In a buffer containing a glycosyltransferase to be measured, are added a sugar nucleotide labelled with $^3H$ or $^{14}C$, a glycoprotein having a terminal to which sugar is to be transfer bound and the necessary metal ions, and activator in amounts controlled to the desired concentrations.

(2) This solution is incubated generally at around 37° C. for several minutes to several hours.

(3) The reaction mixture is treated with trichloroacetic acid or phosphotungstic acid to precipitate the glycoprotein, which is recovered on a filter paper and radioactivity of the transferred sugar is measured.

Next, an example of the measuring method according to an embodiment of the present invention is described.

(1) In a buffer containing a glycosyltransferase is a sugar nucleotide not labelled, a glycoprotein having a terminal to be transfer bound labelled with $^{125}I$, beads having a lectin specific for the above sugar transfer bound immobilized thereon and the necessary metal ions and activator are in amounts controlled to the desired concentrations.

(2) The solution is incubated generally at around 37° C. for several minutes to several hours.

(3) Beads are washed with a buffer, and radioactivity is measured by γ-counter.

Further, an example of the measuring method according to another embodiment of the present invention.

(1) In a buffer containing a glycosyltransferase to be measured are added a sugar nucleotide not labelled, a (monosaccharide) or phospholipid to which its sugar is to be transfer bound, and necessary metal ions and activator in amounts controlled to the desired concentrations.

(2) The solution is incubated generally at around 37° C. for several minutes to several hours.

(3) Further, predetermined amounts of the glycoprotein of the acceptor labelled with $^{125}I$ to which the sugar of the above sugar nucleotide corresponding to its glycosyltransferase has been transferred, and beads having an antibody specific to the above transfer bound sugar immobilized thereon are added.

(4) After standing at room temperature for several hours to permit competitive specific reactions, the beads are washed with pure water, and radioactivity is measured by γ-counter.

The measuring method of the present invention is not limited to these, but various methods may be used. Any method, as described above, comprises using a composition containing a sugar nucleotide not labelled and a substance bound specifically only to the acceptor to which the sugar has been transferred.

The glycosyltransferase to be measured is not necessarily required to be added in the state of a solution, but it may be also added, for example, in a state bound onto a specific immobilized antibody which undergoes specific reaction.

The concentrations of the sugar nucleotide and the acceptor, the composition or pH of the buffer, or additives for the reaction can be controlled to the conditions adequate for the respective transferases. As the labelled substance, there may be mentioned radioisotopes such as $^{125}I$ and $^3H$, enzymes such as horse radish peroxidase, fluorescent substances such as FITC, etc. For the labelled glycoprotein, $^{125}I$ is generally employed, but $^3H$ can be easily employed when a glycolipid is used as the acceptor.

On the other hand, as the substance to be labelled, in addition to acceptor, an acceptor to which sugar is transferred, an antibody, a lectin-like substance may be considered to be employed for a readily feasible method.

In the present invention, any product or a substance specifically bound only to the product may be adsorbed directly or indirectly to a solid phase. As a method of adsorbing it to the solid phase directly, a physical adsorption method may be mentioned. As a method of adsorbing indirectly, the method through avidin-biotin reaction, the method through an antibody, etc. may be mentioned. As the solid phase, materials used for immunoassay, which are well-known in the art can be utilized. There may be mentioned, for example, a nitrocellulose film, an agarose gel, polystyrene beads, etc.

In the present invention, by carrying out the measurement using a substance which is specifically bound only to the product without using a labelled donor, which is different from the method for measuring glycosyltransferase generally known in the art, the following effects can be obtained.

(i) Since a labelled donor which is expensive and unstable is not necessary, there can be accomplished a labelled substance which is cheap. Various labelling methods can be selected in accordance with the use and object.

(ii) Since the width of selection of the labelled substance is increased, sensitivity of measurement is remarkably heightened as compared with the limit of the sensitivity in the conventional method.

Further, by using the substance which is specifically combined only with a product, (iii) an operation of separating an unreacted labelled substance and a product can be accurately carried out within a shorter time as compared with the conventional method, whereby a means of general immunoassay can be applied to a method for measurement of the activity or concentration of glycosyltransferase.

The method of the present invention may be utilized not only in the basic field, but also in the fields of medicine and clinical diagnosis. Particularly, it can be utilized for analysis of an isoenzyme combined with a glycosyltransferase antibody. To date, although much still remains unknown about the kinds of glycosyltransferases, their mechanisms of action, clinical significances, etc., the present invention is expected to contribute to such research.

The present invention is described in more detail by referring to Examples, which are not intended to limit the present invention.

EXAMPLE - 1

In a test tube, the following controlled substances were added.

(1) Galactosyltransferase in milk (Sigma Co.), 0.1 u (corresponding to about 20 μg);

(2) 1 mM/liter of UDP-galactose (Sigma Co.) in 10 μl of distilled water;

(3) 0.2 M/liter of MnCl₂ in 5 μl of distilled water;

(4) 50 μg of Asialoagalactofetuin (prepared according to J. Biol. Chem. Vol. 255, p. 2860 (1960), and $^{125}$I-labelled according to the chloramine-T method, having specific activity of 100,000 cpm);

(5) 85 μl of 100 mM/liter cacodylic acid buffer pH 7.4, 0.01% Triton-X-100 solution;

(6) RCA-I Agarose (EY-Laboratory Co.), 30 μl.

The test tube containing these compositions was incubated at 37° C. for one hour.

After the agrose gel was washed 3 times with 3 ml of 20 mM cacodylic acid, 150 mM KCl, 0.01% Triton-X-100, pH 7.4 (CKT buffer), the gel was measured by γ-counter for one minute.

As the Control, one composition containing no galactose transferase was used.

| Results: | Test sample | 14500 cpm. |
|---|---|---|
| | Control | 320 cpm. |

On the other hand, according to the prior art method in which UDP-[³H] galactose is used and precipitation is effected with 10% trichloroacetic acid, the results were found to be:

| Test sample | 18200 cpm. |
|---|---|
| Control | 280 cpm. |

Thus, it can be appreciated that the method of the present invention can give comparative results and the operation thereof is very simple.

EXAMPLE - 2

This example describes the measuring method of galactosyltransferase isoenzyme (GT-II) which was presented at the 6th Tumor Marker Research Meeting (1986).

(1) 30 μl of the GF-2000 gel (Pierce Co.) having the GT-II specific monoclonal antibody, MAb3872 as described in the above Research Meeting, and (2) 100 μl of a cancer patient's and normal person's serum are left to stand in a test tube at 4° C. overnight.

After the gel was washed 3 times with 3 ml of the CKT buffer (as described above), (1) 100 μM/liter of UDP-galactose in 10 μl of distilled water;

(2) 0.2 M/liter of MnCl₂ in 5 μl of distilled water;

(3) 0.5 mg of N-acetylglucosamine and 0.1 μg of RCA-I; and (4) 85 μl of 100 mM/liter cacodylic acid buffer pH 7.4 0.01% Triton X-100 solution were added, and after incubation at 37° C. for 2 hours, (1) 20 μl of 0.1 M/liter EDTA, 2% BSA CKT buffer solution containing about 2 ng of Asialofetuin, 100,000 cpm of $^{125}$I-labelled product labelled according to the chloramine-T method, and (2) polystyrene beads having an anti-RCA antibody (Vector Co.) immobilized thereon, were added and, after being at room temperature for 2 hours, the beads were washed with pure water and the radioactivity was measured.

| Ovarian tumor serum | | Normal person serum | | Control test sample | | | | |
|---|---|---|---|---|---|---|---|---|
| No. | cpm | mU/mL | No. | cpm | mU/mL | No. | cpm | mU/mL |
| 1 | 5310 | 445 | 1 | 1010 | 70 | 1 | 280 | 0 |
| 2 | 1750 | 130 | 2 | 930 | 55 | 2 | 820 | 50 |
| 3 | 3840 | 340 | 3 | 540 | 35 | 3 | 1450 | 100 |
| 4 | 2750 | 195 | 4 | 1930 | 140 | 4 | 2880 | 200 |
| 5 | 4830 | 460 | 5 | 1270 | 90 | 5 | 4510 | 400 |
| 6 | 10540 | 1040 | 6 | 1640 | 115 | 6 | 7650 | 800 |
| 7 | 7350 | 785 | | | | | | |
| 8 | 1450 | 100 | | | | | | |
| 9 | 2920 | 215 | | | | | | |
| 10 | 3050 | 230 | | | | | | |

From the above results, the method of the present invention demonstrates that it has sensitivity and specificity comparable to the measuring method of GT-II of the prior art and can be a measuring method of tumor marker which is more practical than the prior method.

EXAMPLE - 3

In a test tube, the following controlled substances were added.

(1) PBS solution containing 10 μl of galactosyltransferase extracted from cancer tissue of an ovaian cancer patient, or a solution of the above diluted with PBS;

(2) 0.5 mg of N-acetylglucosamine and 100 μM/liter of UDP-galactose in 10 μl of distilled water;

(3) 170 μl of buffer (100 mM/liter of cacodylic acid, 10 mM/liter of MnCl₂, 0.01% of Triton-X-100, pH 7.4);

(4) a 10 μl solution of Galβ1-4GluNAc-BSA (available from Pierce Co., which is $^{125}$I-labelled according to the chloriamine-T method (2 ng of a labelled body having a specific activity of about 100,000 cpm, 2% BSA and 100 mM/liter of cacodylic acid, pH 7.4 solution);

(5) polystyrene beads immobilized a monoclonal antibody LB2 (J. Biol. Chem., 256 (21), pp. 10967 to 10972 (1981)) which is specifically combined with Galβ1-4GluNac (N-acetyllactosamine).

After the test tube containing these compositions was incubated at 37° C. for one hour, the beads were washed 3 times with distilled water and the radioactivity of the beads was measured.

As the comparative example to the present invention, the following measurement was carried out in the same manner as in the above.

(1) 10 μl of the aforesaid galactosyltransferase solution;

(2) 0.5 mg of N-acetylglucosamine and 100 μM/liter of UDP-galactose labelled by tritium (³H) and having a specific activity of about 100,000 cpm in 10 μl of distilled water;

(3) 170 μl of the above buffer;

(4) the above polystyrene beads with immobilized monoclonal antibody.

After the test tube containing these compositions was incubated at 37° C. for one hour, the beads were washed 3 times with distilled water and the radioactivity of the beads was measured by liquid scintilation measurement.

The results are shown in FIGS. 1 (the present invention) and 2 (comparative sample), respectively. As seen from the figures, the method of the present invention can be measured at a dilution of 1:100 and it can be understood that the method of the present invention is increased about 5 to 10-fold in sensitivity of measurement as compared with that of the conventional method.

We claim:

1. A method for directly measuring a concentration of a galactosyltransferase by measuring an activity of said galactosyltransferase in a serum, comprising:

adding a non-labeled uridine diphosphate-sugar having a first sugar, a non-labeled substance, a labeled acceptor having a second sugar and a non-labeled acceptor to which said first sugar is to be transferred by said galactosyltransferase in said serum, wherein said non-labeled acceptor is selected from the group consisting of monosaccharides, oligosaccharides, glycoproteins and glycolipids, said non-labeled substance is a lectin or an antibody and is specifically bound only to the non-labeled acceptor to which the sugar has been transferred, and said labeled acceptor comprises a radioisotope, an enzyme or a fluorescent substance, said non-labeled substance is immobilized to a solid phase;

incubating said serum to effect enzymatic reaction, washing said solid phase; and measuring said non-labeled acceptor to which the sugar has been transferred on said solid phase.

2. The method for measuring a glycosyltransferase according to claim 1, wherein said labeled acceptor is labeled by a radioisotope.

3. The method for measuring a glycosyltransferase according to claim 2, wherein said radioisotope is $^{125}I$.

4. The method for measuring a glycosyltransferase according to claim 2, wherein said radioisotope is $^{3}H$.

5. The method for measuring a glycosyltransferase according to claim 1, wherein said labeled acceptor is labeled by an enzyme or a fluorescent substance.

6. The method for measuring a galactosyltransferase according to claim 1, wherein said radioisotope is $^{125}I$.

7. The method for measuring a galactosyltransferase according to claim 1, wherein said non-labeled substance which is capable of binding specifically to the non-labeled acceptor to which the sugar has been transferred is a monoclonal antibody.

8. The method for measuring a galactosyltransferase according to claim 1, wherein said substance which is capable of binding specifically to the non-labeled acceptor to which the sugar has been transferred is RCA or a monoclonal antibody which is specifically bound only to a sugar chain containing non-reducing terminal galactose.

9. The method for measuring a galactosyltransferase according to claim 1, wherein said non-labeled substance which is capable of binding specifically to the non-labeled acceptor to which the sugar has been transferred is directly or indirectly adsorbed to said solid phase.

10. The method for measuring a galactosyltransferase according to claim 1, wherein said non-labeled substance which is capable of binding specifically to the non-labeled acceptor to which the sugar has been transferred is RCA or a monoclonal antibody which is specifically bound only to a sugar chain containing non-reducing terminal galactose, and is directly or indirectly adsorbed to said solid phase.

* * * * *